(12) United States Patent
Yang et al.

(10) Patent No.: US 12,027,240 B2
(45) Date of Patent: Jul. 2, 2024

(54) ELECTRONIC DEVICE, AND COMPUTER-READABLE STORAGE MEDIUM

(71) Applicant: Tencent Technology (Shenzhen) Company Limited, Shenzhen (CN)

(72) Inventors: Yaodong Yang, Shenzhen (CN); Hongyao Tang, Shenzhen (CN); Guangyong Chen, Shenzhen (CN); Shengyu Zhang, Shenzhen (CN); Changyu Hsieh, Shenzhen (CN); Jianye Hao, Shenzhen (CN)

(73) Assignee: TENCENT TECHNOLOGY (SHENZHEN) COMPANY LIMITED, Shenzhen (CN)

(*) Notice: Subject to any disclaimer, the term of this patent is extended or adjusted under 35 U.S.C. 154(b) by 351 days.

(21) Appl. No.: 17/522,702

(22) Filed: Nov. 9, 2021

(65) Prior Publication Data

US 2022/0068442 A1    Mar. 3, 2022

Related U.S. Application Data

(63) Continuation of application No. PCT/CN2020/126805, filed on Nov. 5, 2020.

(30) Foreign Application Priority Data

Mar. 5, 2020  (CN) .......................... 202010148735.4

(51) Int. Cl.
*G16C 20/50* (2019.01)
*G06F 30/27* (2020.01)
*G16C 20/10* (2019.01)

(52) U.S. Cl.
CPC ............. *G16C 20/50* (2019.02); *G06F 30/27* (2020.01); *G16C 20/10* (2019.02)

(58) Field of Classification Search
CPC .......... G16C 20/50; G06F 30/27; G06N 3/044
(Continued)

(56) References Cited

U.S. PATENT DOCUMENTS

| 2019/0147370 A1 | 5/2019 | Botea et al. |
| 2019/0244099 A1 | 8/2019 | Schaul et al. |
| 2020/0050947 A1 | 2/2020 | Kishimoto et al. |

FOREIGN PATENT DOCUMENTS

| CN | 107632295 A | 1/2018 |
| CN | 108304918 A | 7/2018 |

(Continued)

OTHER PUBLICATIONS

Tencent Technology, KR Office Action, Korean Patent Application No. 10-2021-7028575, Feb. 15, 2023, 17 pgs.
(Continued)

*Primary Examiner* — Thinh T Nguyen
(74) *Attorney, Agent, or Firm* — Morgan, Lewis & Bockius LLP (57) ABSTRACT

Embodiments of this application relate to a retrosynthesis processing method and apparatus, an electronic device, and a computer-readable storage medium. A retrosynthesis processing method is performed by a computer device. The method includes determining molecular representation information of a target molecule. The method includes inputting the molecular representation information into a target neural network. The method includes performing, via the target neural network, retrosynthesis processing on the target molecule based on the molecular representation information of the target molecule, to obtain a respective retrosynthesis reaction of the target molecule for each step of the retrosynthesis processing. The target neural network is obtained by training a predetermined neural network according to a sample cost dictionary that is generated by concurrently performing retrosynthesis reaction training on each of
(Continued)

a plurality of sample molecules, and the respective retrosynthesis reaction is performed according to a preset retrosynthesis reaction architecture.

10 Claims, 5 Drawing Sheets

(58) Field of Classification Search
USPC .......................................................... 703/12
See application file for complete search history.

(56) References Cited

FOREIGN PATENT DOCUMENTS

| CN | 109285589 A | 1/2019 |
|---|---|---|
| CN | 109299781 A | 2/2019 |
| CN | 109872780 A | 6/2019 |
| CN | 110634539 A | 12/2019 |
| JP | 2005270909 A | 10/2005 |
| WO | WO 2019079580 A1 | 4/2019 |
| WO | WO 2020023650 A1 | 1/2020 |

OTHER PUBLICATIONS

Tencent Technology, JP Office Action, Japanese Patent Application No. 2021-545366, Sep. 13, 2022, 6 pgs.
Tencent Technology, WO, PCT/CN2020/126805, Jan. 29, 2021, 4 pgs.
Tencent Technology, IPRP, PCT/CN2020/126805, Sep. 6, 2022, 5 pgs.
A. Filipa de Almeida et al., "Synthetic Organic Chemistry Driven by Artificial Intelligence", Nature Reviews Chemistry, vol. 3, No. 10, XP037237652, 16 pgs.
Connor W. Coley et al., "Machine Learning in Computer-Aided Synthesis Planning", Accounts of Chemical Research, 2018, vol. 51, No. 5, XP055660945, 9 pgs.
H.C. Stephen Chan et al., "Advancing Drug Discovery via Artificial Intelligence", Trends in Pharmacological Sciences, vol. 40, No. 8, XP085747755, 13 pgs.
Marwin H. S. Segler et al., "Neural-Symbolic Machine Learning for Retrosynthesis and Reaction Prediction", Chemistry—A European Journal, vol. 23, 6 pgs.
Marwin H. S. Segler et al., "Planning Chemical Syntheses with Deep Neural Networks and Symbolic AI", Nature, 2018, vol. 555, No. 7698, XP093064661, 16 pgs.
Marwin Segler et al., "Towards "Alphachem": Chemical Synthesis Planning with Tree Search and Deep Neural Network Policies", 2017, arXiv.org, XP093064081, 4 pgs.
Shoichi Ishida et al., "Prediction and Interpretable Visualization of Retrosynthetic Reactions Using Graph Convolutional Networks", Journal of Chemical Information and Modeling, 2019, vol. 59, No. 12, XP093063947, 8 pgs.
Shuangjia Zheng et al., "Predicting Retrosynthetic Reactions Using Self-Corrected Transformer Neural Networks", Journal of Chemical Information and Modeling, Jan. 27, 2020, vol. 60, No. 1, 9 pgs.
Tencent Technology, Extended European Search Report and Supplementary Search Report, EP20922890.7, Jul. 26, 2023, 15 pgs.
Tencent Technology, ISR, PCT/CN2020/126805, Jan. 29, 2021, 2 pgs.
John S.Schreck et al., "Learning Retrosynthetic Planning Through Simulated Experience", ACS Central Science, May 31 2019, 12 pgs.
Li Wei et al., "Deep Learning in Drug Design and Discovery", Acta Pharmaceutica Sinica 2019, Apr. 9, 2019, 7 pgs.
Wojciech Jaworski et al., "Automatic Mapping of Atoms Across Both Simple and Complex Chemical Reactions", Nature Communications, Mar. 29, 2019, 11 pgs.

ELECTRONIC DEVICE, AND COMPUTER-READABLE STORAGE MEDIUM

CROSS REFERENCE TO RELATED APPLICATIONS

This application is a continuation application of PCT Patent Application No. PCT/CN2020/126805, entitled "RETROSYNTHESIS PROCESSING METHOD AND APPARATUS, ELECTRONIC DEVICE, AND COMPUTER-READABLE STORAGE MEDIUM" filed on Nov. 5, 2020, which claims priority to Chinese Patent Application No. 202010148735.4, filed with the State Intellectual Property Office of the People's Republic of China on Mar. 5, 2020, and entitled "RETROSYNTHESIS PROCESSING METHOD AND APPARATUS, ELECTRONIC DEVICE, AND COMPUTER-READABLE STORAGE MEDIUM", all of which are incorporated herein by reference in their entirety.

FIELD OF THE TECHNOLOGY

This application relates to computer information processing technologies, and in particular, to a retrosynthesis processing method and apparatus, an electronic device, and a computer-readable storage medium.

BACKGROUND OF THE DISCLOSURE

Since the 1990s, the development of disciplines such as computer technologies, computational chemistry, molecular biology, and bioinformatics has greatly promoted the progress of computer-assisted chemical drug molecule retrosynthesis processing. A large quantity of methods for computer-aided chemical drug molecule retrosynthesis processing emerge, for example, retrosynthesis design based on Monte Carlo Tree Search.

However, it is found in specific implementation that a retrosynthesis processing method in the related art has low accuracy of calculated retrosynthesis reaction. As a result, a retrosynthesis route is not optimized and effective enough.

SUMMARY

To resolve at least one of the technical defects, embodiments of this application provide the following technical solutions.

An embodiment of this application provides a retrosynthesis processing method, including:
  determining molecular representation information of a target molecule;
  inputting the molecular representation information into a target neural network, and performing retrosynthesis processing on the target molecule based on the molecular representation information of the target molecule using the target neural network, to obtain a respective retrosynthesis reaction of the target molecule for each step of the retrosynthesis processing,
  the target neural network is obtained by training a predetermined neural network according to a sample cost dictionary that is generated by concurrently performing retrosynthesis reaction training on each of a plurality of sample molecules (e.g., concurrently training each of the sample molecules multiple times), and the respective retrosynthesis reaction is performed according to a preset retrosynthesis reaction architecture.

An embodiment of this application provides a retrosynthesis processing apparatus, including:
  a determining module, configured to determine molecular representation information of a target molecule; and
  a processing module, configured to input the molecular representation information into a target neural network, and perform retrosynthesis processing on the target molecule based on the molecular representation information of the target molecule by using the target neural network, to obtain a retrosynthesis reaction in each step of the retrosynthesis processing performed on the target molecule, the target neural network being obtained by training a predetermined neural network according to a generated sample cost dictionary, the sample cost dictionary being generated by performing a plurality of times of retrosynthesis reaction training on each of a plurality of sample molecules concurrently according to a preset retrosynthesis reaction architecture.

An embodiment of this application provides a computer device (e.g., an electronic device), including a memory, a processor, and a computer program stored on the memory and executable by the processor, the processor, when executing the program, implementing the foregoing retrosynthesis processing method.

An embodiment of this application provides a non-transitory computer-readable storage medium, storing a computer program, the program, when executed by a processor, causing the processor to implement the foregoing retrosynthesis processing method.

According to the embodiments of this application, the plurality of times of retrosynthesis reaction training are performed on each of the plurality of sample molecules concurrently according to the preset retrosynthesis reaction architecture, thereby implementing a distributed parallel computing scheme for training optimization of the sample cost dictionary, which greatly reduces the time for training optimization of the sample cost dictionary, increases the calculation speed and improves iteration efficiency, and greatly reduces the time for calculation of a value function strategy. It is also ensured that the target neural network can provide an effective retrosynthesis route and accurately obtain the retrosynthesis reaction in each step when performing retrosynthesis processing on the target molecule, thereby implementing the automated design of the retrosynthesis route.

BRIEF DESCRIPTION OF THE DRAWINGS

The foregoing and/or additional aspects and advantages of the embodiments of this application will become more obvious and easier to understand from the following descriptions of the embodiments with reference to the accompanying drawings.

DESCRIPTION OF EMBODIMENTS

Embodiments of this application are described in detail below, and examples of the embodiments are shown in accompanying drawings, where the same or similar elements or the elements having same or similar functions are denoted by the same or similar reference numerals throughout the description. The embodiments that are described below with reference to the accompany drawings are exemplary, and are only used to interpret this application and cannot be construed as a limitation to this application.

A person skilled in the art may understand that, the singular forms "a", "an", and "the" used herein may include the plural forms as well, unless the context clearly indicates otherwise. It is to be further understood that, the terms "include" and/or "comprise" used in this specification of this application refer to the presence of stated features, integers, steps, operations, elements, and/or components, but do not preclude the presence or addition of one or more other features, integers, steps, operations, elements, components, and/or combinations thereof. It is to be understood that, when an element is "connected" or "coupled" to another element, the element may be directly connected to or coupled to another element, or an intermediate element may exist. In addition, the "connection" or "coupling" used herein may include a wireless connection or a wireless coupling. The term "and/or" used herein includes all of or any of units and all combinations of one or more related listed items.

To make objectives, technical solutions, and advantages of the embodiments of this application clearer, the following further describes in detail implementations of this application with reference to the accompanying drawings.

The embodiments of this application provide a retrosynthesis processing method and apparatus, an electronic device, and a computer-readable storage medium to resolve the preceding technical problems in the related art.

To better understand and describe the solutions in the embodiments of this application, the following briefly describes some technical terms involved in the embodiments of this application.

a. Monte Carlo tree search (MCTS) is a general term for a type of tree search algorithm that can effectively resolve some problems of exploring a huge space. When the problem to be resolved is a probability of occurrence of a specific event or an expected value of a specific random variable, the frequency of this event or a mean value of this random variable may be obtained by using a specific "test" method, and serve as the solution to the problem.

b. Retrosynthesis analysis is an important method for resolving an organic synthesis route, and is also the simplest and most basic method for design of the organic synthesis route. The essence is the separation of a target molecule. The structure of the target molecule is gradually separated into simpler and easier-to-synthesize precursors and raw materials through analysis of the structure of the target molecule, thereby completing the design of the route.

c. A reaction template describes the process of a type of chemical reaction, including the breaking of old chemical bonds and the formation of new chemical bonds.

d. A reaction zone is an active zone where chemical bonds and atoms change when a chemical reaction occurs. The active zone may be a preset zone. For example, a zone where a single bond changes to a double bond in chemical bonds is the active zone, that is, the reaction zone.

e. A precursor is a compound added to a culture medium, and is a type of substance with small molecules that can be directly incorporated into a product molecule during biosynthesis without a great change in its structure while increasing the yield of the product.

f. The reinforcement learning emphasizes how to act based on an environment to maximize expected benefits. It is concerned with how an intelligent agent gradually forms an expectation of a stimulus under the stimulation of a reward or a punishment given by the environment and generates the habitual behavior through which the greatest benefit can be obtained.

A Markov decision process (MDP) is a mathematical model of sequential decision and is used for simulating a random strategy and returns that the intelligent agent can implement in an environment in which a system state has a Markov property. The MDP is constructed based on a set of interactive objects, that is, the intelligent agent and the environment, including elements such as states, actions, strategies, and rewards. In simulation of the MDP, the intelligent agent perceives the current system state and implements actions on the environment according to the strategy, thereby changing the state of the environment and obtaining rewards. The accumulation of rewards over time is referred to as rewards.

The following describes the technical solutions of the embodiments of this application and how to resolve the foregoing technical problems according to the technical solutions of the embodiments of this application in detail by using the embodiments of this application. The following several specific embodiments may be combined with each other, and the same or similar concepts or processes may not be described repeatedly in some embodiments. The following describes the embodiments of this application with reference to the accompanying drawings.

It is found during specific implementation that the retrosynthesis processing method in the related art is usually completed by a single computer device. It takes a very long time to calculate the value function strategy. Specifically, often millions of hours of single-core operations are required. In addition, accuracy of calculated costs of retrosynthesis reactions is relatively low. As a result, a retrosynthesis route is not optimized and effective enough.

In order to resolve the preceding problems, an embodiment of this application provides a retrosynthesis processing method. A sample cost dictionary is generated by performing a plurality of times of retrosynthesis reaction training on each of a plurality of sample molecules concurrently according to a preset retrosynthesis reaction architecture, thereby implementing a distributed parallel computing scheme for training optimization of the sample cost dictionary, which greatly reduces the time for training optimization of the sample cost dictionary, increases the calculation speed and improves iteration efficiency, so that a value function strategy can be quickly obtained according to the sample cost dictionary, greatly reducing the time for calculation of the value function strategy. The predetermined neural network is trained according to the pre-generated sample cost dictionary to obtain a target neural network, so that costs of retrosynthesis reactions can be fitted through the neural network to obtain a respective retrosynthesis reaction in each step of the retrosynthesis processing. In addition, it is ensured that the target neural network can provide an effective retrosynthesis route when performing retrosynthesis processing on the target molecule, to accurately obtain the retrosynthesis reaction in each step, thereby implementing the automated design of the retrosynthesis route. Moreover, the pre-generated cost dictionary is mapped to the neural network, which can make full use of the fitting ability and generalization ability of the neural network, so that a reasonable and effective retrosynthesis route can be designed for new molecules, and the retrosynthesis reaction in each step can be quickly obtained.

The electronic device provided by the embodiments of this application for implementing the retrosynthesis processing method described below may be various types of terminal devices or servers. The server may be an independent physical server, or may be a server cluster or a distributed computing system including a plurality of physical servers, or may be a cloud server that provides cloud computing services. The terminal may be a smart phone, a tablet computer, a notebook computer, a desktop computer, a smart speaker, a smart watch, or the like, which is not limited thereto. The terminal and the server may be directly or indirectly connected in a wired or wireless communication manner. This is not limited in this embodiment of this application.

The retrosynthesis processing method provided in the embodiments of this application may be separately implemented by the terminal or the server, or may be collaboratively implemented by the terminal and the server. For example, when the terminal independently performs the retrosynthesis processing method described below when acquiring molecular representation information of a target molecule, to obtain a retrosynthesis reaction in each step of retrosynthesis processing on the target molecule. Researchers perform subsequent molecular studies based on the retrosynthesis reaction in each step of the retrosynthesis processing performed on the target molecule. When the molecular representation information of the target molecule is obtained, the terminal transmits the molecular representation information of the target molecule to the server. After receiving the molecular representation information of the target molecule, the server performs the retrosynthesis processing to obtain the retrosynthesis reaction in each step of the retrosynthesis processing performed on the target molecule, and transmits the retrosynthesis reaction in the step to the terminal. The researchers perform subsequent molecular studies based on the retrosynthesis reaction in the step of the retrosynthesis processing performed on the target molecule.

Figure 1A:
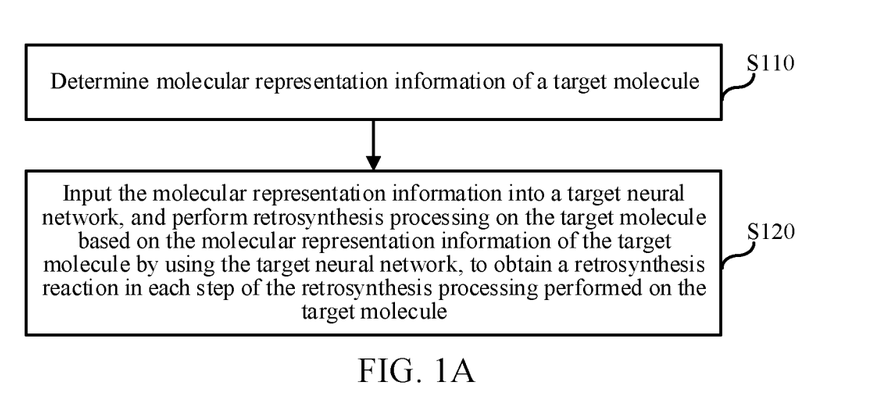
FIG. 1A and FIG. 1B are schematic flowcharts of a retrosynthesis processing method according to an embodiment of this application.

An embodiment of this application provides a retrosynthesis processing method. The method is performed by a computer device (e.g., an electronic device). The computer device may be a terminal or a server system. The terminal may be a desktop device or a mobile terminal. The server may be an independent physical server, a physical server cluster, or a virtual server. As shown in FIG. 1A, the method includes the following steps: step S110: Determine molecular representation information of a target molecule: step S120: Input the molecular representation information into a target neural network, and perform retrosynthesis processing on the target molecule based on the molecular representation information of the target molecule by using the target neural network, to obtain a retrosynthesis reaction in each step of the retrosynthesis processing performed on the target molecule. The target neural network is obtained by training a predetermined neural network according to a pre-generated sample cost dictionary. The sample cost dictionary is generated by performing a plurality of times of retrosynthesis reaction training on each of a plurality of sample molecules concurrently according to a preset retrosynthesis reaction architecture.

As an example, the target neural network is not limited to any type, for example, a convolutional neural network (CNN), a recurrent neural network (RNN), or a deep neural network (DNN).

For example, the above target molecule may be a chemical drug molecule, which may be a currently known chemical drug molecule, or may be a new type of chemical drug molecule that has not appeared before (also referred to as a new type of molecule).

For example, the molecular representation information generally refers to molecular information that can be used for retrosynthesis analysis of chemical drug molecules, and a retrosynthesis reaction in each step of the retrosynthesis processing can be obtained according to the molecular representation information.

In this embodiment of this application, the sample cost dictionary is generated by performing the plurality of times of retrosynthesis reaction training on each of the plurality of sample molecules concurrently according to the preset retrosynthesis reaction architecture. In other words, the sample cost dictionary is generated by performing the plurality of times of retrosynthesis reaction training on each of the plurality of sample molecules concurrently according to the preset retrosynthesis reaction architecture. The sample cost dictionary is updated or optimized every time the retrosynthesis reaction training is performed, so that the optimal sample cost dictionary is obtained through the plurality of times of retrosynthesis reaction training. That is, the sample cost dictionary is an optimized and complete cost dictionary obtained through the plurality of times of retrosynthesis reaction training.

For example, the target neural network is obtained by training the predetermined neural network according to the pre-generated sample cost dictionary. After the optimal sample cost dictionary is obtained through the plurality of times of retrosynthesis reaction training, the predetermined neural network is then trained according to the sample cost dictionary to obtain the target neural network, thereby ensuring the accuracy of performing retrosynthesis processing on the target molecule by using the target neural network.

According to the retrosynthesis processing method provided in this embodiment of this application, the sample cost dictionary is generated by performing the plurality of times of retrosynthesis reaction training on each of the plurality of sample molecules concurrently according to the preset retrosynthesis reaction architecture, thereby implementing a distributed parallel computing scheme for training optimization of the sample cost dictionary, which greatly reduces the time for training optimization of the sample cost dictionary, increases the calculation speed and improves iteration efficiency, so that a value function strategy (a cost dictionary) can be quickly obtained according to the sample cost dictionary, greatly reducing the time for calculation of the value function strategy. The predetermined neural network is trained according to the pre-generated sample cost dictionary to obtain the target neural network, so that costs of retrosynthesis reactions can be fitted through the neural network to obtain a retrosynthesis reaction in each step. In addition, it is ensured that the target neural network can provide an effective retrosynthesis route when performing retrosynthesis processing on the target molecule, to accurately obtain the retrosynthesis reaction in each step, thereby implementing the automated design of the retrosynthesis route. Moreover, the pre-generated cost dictionary is mapped to the neural network, which can make full use of the fitting ability and generalization ability of the neural network, so that a reasonable and effective retrosynthesis route can be designed for new molecules, and the retrosynthesis reaction in each step can be obtained.

For example, the molecular representation information may be a simplified molecular-input line-entry system, or may be a molecular graph. The simplified molecular-input line-entry system is a system that clearly describes a molecular structure by using ASCII strings, that is, describing a three-dimensional chemical structure by using a string of characters. A charge density, free valence, and a bond level are all closely related to the properties of a molecule. On a carbon skeleton of a conjugated molecule, these Shockel quantities are expressed to form a molecular graph. Properties of nodes and edges commonly used in the molecular graph are shown in Table 1 below.

TABLE 1

Properties of nodes and edges commonly used in molecular graph

| Type | Property | Description |
|---|---|---|
| Node | Atom type | Carbon, nitrogen, oxygen, hydrogen, fluorine, sulfur, chlorine, etc. (one-hot encoding) |
|  | Atomic number | Quantity of protons (integer) |
|  | Positive valence | Receiving electron (binary) |
|  | Negative valence | Contribution electron (binary) |
|  | Aromatic | In aromatics (binary) |
|  | Hybridization | sp, sp2, sp3 (one-hot encoding or zero) |
|  | Quantity of hydrogen atoms | (integer) |
| Edge | Type of chemical bond | Single bond, double bond, triple bond, aromatic (one-hot encoding) |
|  | Distance between atoms | (real number) |

A hybridization difference among sp, sp2, and sp3 mainly lies in different configurations of electron clouds and the quantity of atoms that are connected to a central atom. An electron cloud formed by an sp hybrid orbital is linear, and a central atom is connected to 2 atoms (or lone pair electrons). An electron cloud formed by an sp2 hybrid orbital is in a regular triangle configuration, and a central atom is connected to 3 atoms (or lone pair electrons). An electron cloud formed by an sp3 hybrid orbital is in a regular tetrahedral configuration, and a central atom is connected to 4 atoms (or lone pair electrons).

This embodiment of this application is described below in detail by using an example in which the molecular representation information is the simplified molecular-input line-entry system.

In this embodiment of this application, in the process of performing the plurality of times of retrosynthesis reaction training on each of the plurality of sample molecules concurrently according to the preset retrosynthesis reaction architecture to generate the sample cost dictionary, the plurality of times of retrosynthesis reaction training may be performed on the plurality of sample molecules concurrently according to the preset retrosynthesis reaction architecture by using a predetermined work cluster including a plurality of workload nodes and at least one control node, to generate the sample cost dictionary.

For example, the predetermined work cluster may be a computing cluster including a plurality of computing devices, which are closely collaborated with each other to complete computing work. In a certain sense, the predetermined work cluster may be regarded as a super computing device. The predetermined work cluster may be used for improving the computing speed and/or reliability of a single computing device. A single computing device in the predetermined work cluster is referred to as a node. Nodes are connected to each other by using a local area network, or are connected in another possible manner, which is not limited in the embodiments of this application. The single computing device herein is not limited to a single computer, a single virtual machine, or the like, and may be composed of several computers, virtual machines, or the like.

For example, the predetermined work cluster includes one or more control nodes and a plurality of workload nodes (or referred to as computing nodes). The control node is responsible for the management and control of the entire cluster. Basically, all control commands of the predetermined work cluster are transmitted to the control node. The control node is responsible for a specific performing process. In addition to the control node, other computing devices in the predetermined work cluster are referred to as workload nodes. Each of the workload nodes is allocated with some workloads by the control node. When a workload node goes down, the workload on the workload node is transferred to another workload node by the control node.

Figure 1B:
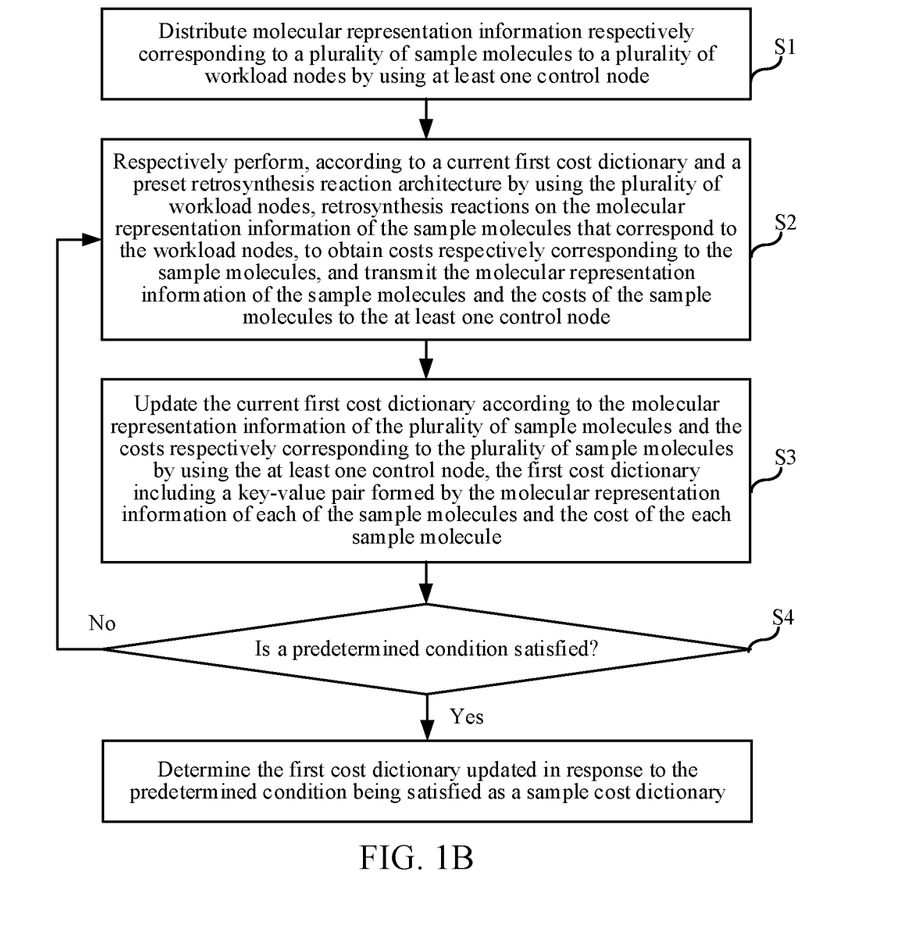

In this embodiment of this application, as shown in FIG. 1B, in the process of performing the plurality of times of retrosynthesis reaction training on each of the plurality of sample molecules concurrently according to the preset retrosynthesis reaction architecture by using the predetermined work cluster, to generate a sample cost dictionary, the following specific processing steps may be performed.

Step S1: Distribute respective molecular representation information corresponding to a plurality of sample molecules to a plurality of workload nodes by using at least one control node.

Step S2: Respectively perform, according to a current first cost dictionary and the preset retrosynthesis reaction architecture by using the plurality of workload nodes, retrosynthesis reactions on the molecular representation information of the sample molecules that respectively correspond to the workload nodes, to obtain costs respectively corresponding to the sample molecules, and transmit the molecular representation information of the sample molecules and the cost of the sample molecules to the at least one control node.

Step S3: Update the current first cost dictionary according to the molecular representation information of the plurality of sample molecules and the costs respectively corresponding to the plurality of sample molecules by using the at least one control node, the first cost dictionary including a key-value pair formed by the molecular representation information of each of the sample molecules and the cost of the sample molecule.

Step S4: Iteratively perform step S2 and step S3 until a predetermined condition is satisfied, and determine the first cost dictionary updated in response to the predetermined condition being satisfied as the sample cost dictionary.

Step S1 is not necessarily performed during each training. Therefore, when the control node distributes the molecular representation information respectively corresponding to the plurality of sample molecules to the plurality of workload nodes, redistribution may or may not be performed. Certainly, when a workload node goes down, redistribution can be performed through the control node again. That is, the molecular representation information respectively corresponding to the plurality of sample molecules is distributed again to a plurality of workload nodes that do not go down.

For example, in the process of performing the plurality of times of retrosynthesis reaction training on each of the plurality of sample molecules concurrently according to the preset retrosynthesis reaction architecture by using the predetermined work cluster, to generate the sample cost dictionary, it is necessary to transmit simplified molecular-input line-entry systems respectively corresponding to the plurality of sample molecules to the control node in the predetermined work cluster. The control node then reasonably distributes the simplified molecular-input line-entry systems of the plurality of sample molecules to the plurality of different workload nodes according to load status of the workload nodes, so that each of the workload nodes is responsible for respectively performing retrosynthesis reactions on the simplified molecular-input line-entry systems of some of the sample molecules according to the preset retrosynthesis reaction architecture.

Figure 1C:
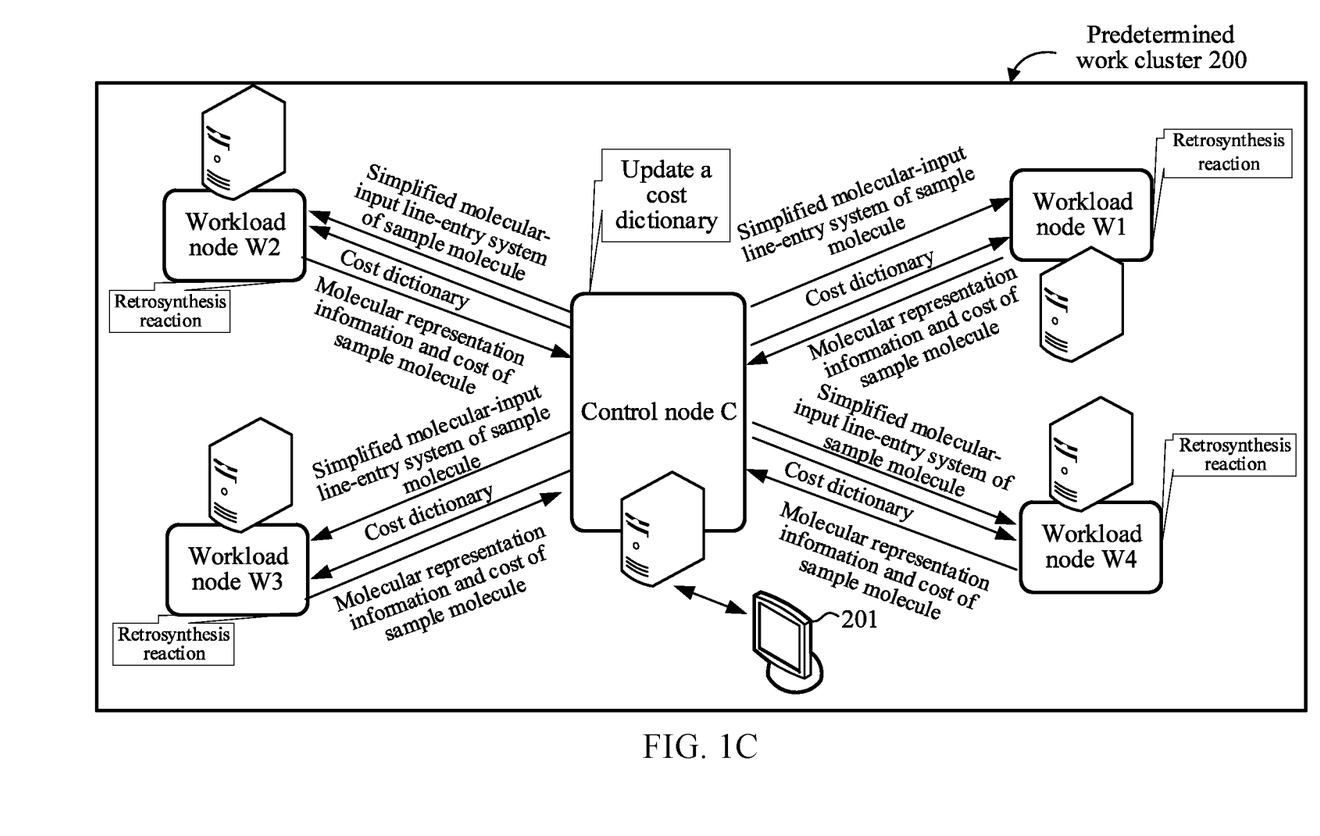
FIG. 1C is a schematic diagram of a predetermined work cluster architecture according to an embodiment of this application.

As shown in FIG. 1C, assuming that there is one control node C and four workload nodes (namely, W1, W2, W3, and W4) in a predetermined work cluster 200, and there are a total of 20 sample molecules (namely, S1, S2, . . . , S20), simplified molecular-input line-entry systems of the 20 sample molecules are transmitted to the control node C. The control node C reasonably distributes the simplified molecular-input line-entry systems of a plurality of sample molecules to a plurality of different workload nodes according to load status of W1, W2, W3, and W4. For example, simplified molecular-input line-entry systems of four sample molecules (such as S1, S2, S3, and S4) are distributed to the workload node W1, and simplified molecular-input line-entry systems of five sample molecules (such as S12, S13, . . . , S16) are distributed to the workload node W2, simplified molecular-input line-entry systems of seven sample molecules (such as S5, S6, . . . , S11) are distributed to the workload node W3, and simplified molecular-input line-entry systems of four sample molecules (such as S17, S18, S19, and S20) are distributed to the workload node W4. After the control node completes the training of the sample cost dictionary, the control node C may transmit the sample cost dictionary to a terminal 201 to display the structure of the sample cost dictionary on a display interface of the terminal 201 for researchers to conduct subsequent research.

In this embodiment of this application, after the molecular representation information respectively corresponding to the plurality of sample molecules is distributed to the plurality of workload nodes by using the control node, each of the workload nodes receives a message about its own load, and performs, according to the received message and the preset retrosynthesis reaction architecture, the retrosynthesis reaction on the simplified molecular-input line-entry system of the sample molecule for which the workload node is responsible.

For example, as shown in FIG. 1C, before the workload node performs, according to the preset retrosynthesis reaction architecture, the retrosynthesis reaction on the simplified molecular-input line-entry system of the sample molecule for which the workload node is responsible, the control node may first transmit the current first cost dictionary to the workload node. The workload node performs, according to the received current first cost dictionary and the preset retrosynthesis reaction architecture, the retrosynthesis reaction on the simplified molecular-input line-entry system of the sample molecule for which the workload node is responsible, to obtain the cost corresponding to each of the sample molecules. The preset retrosynthesis reaction architecture may be a multi-step retrosynthesis route based on deep reinforcement learning shown in FIG. 2, and dmax=10 in FIG. 2 indicates that a maximum depth is 10.

For example, for step S2 in the first training, the current first cost dictionary is a preset initial cost dictionary. The initial cost dictionary is not particularly accurate and is continuously optimized and updated in the process of a plurality of times of subsequent retrosynthesis reaction training, and finally an optimized cost dictionary is obtained (that is, the sample cost dictionary). For the subsequent second training, the third training, and the last training, the current first cost dictionary is a cost dictionary updated according to a previous training of the current training.

For example, after obtaining the cost corresponding to each sample molecule for which the workload node is responsible, each workload node may first transmit the molecular representation information of the sample molecule and the cost of the sample molecule to the control node. After receiving the molecular representation information of the sample molecules and the costs of the sample molecules returned by the workload nodes, the control node updates the current first cost dictionary according to the molecular representation information of the sample molecules and the costs of the sample molecules, to obtain the updated first cost dictionary, and use the updated first cost dictionary as a current first cost dictionary for the next training. The first cost dictionary includes a key-value pair formed by the molecular representation information of each of the sample molecules and the cost of each sample molecule. That is, in the current first cost dictionary, the molecular representation information of each sample molecule is in a one-to-one correspondence with the cost of each sample molecule.

For example, when the predetermined condition is met after the current training, the training is not continued. That is, the training is ended. The first cost dictionary updated according to the molecular representation information of the plurality of sample molecules obtained according to the current training and the costs of the plurality of sample molecules is used as the final sample cost dictionary.

The training process of the above steps S2, S3 and S4 is specifically described by using an example in which the molecular representation information respectively corresponding to the plurality of sample molecules is not redistributed in a subsequent training process after the control node distributes the molecular representation information to the plurality of workload nodes.

It is assumed that there are 20 sample molecules (respectively S1, S2, . . . , S20), the workload node W1 is responsible for the four sample molecules S1, S2, S3, and S4, the workload node W2 is responsible for the five sample molecules S12, S13, . . . , and S16, the workload node W3 is responsible for the seven sample molecules S5, S6, . . . , S11, and the workload node W4 is responsible for the four sample molecules S17, S18, S19, and S20.

During the first training, the current first cost dictionary is a preset initial cost dictionary (denoted as P0), and P0 may be first transmitted to each of the workload nodes W1, W2, W3, and W4. Next, the workload node W1 respectively performs, according to the cost dictionary P0 and the preset retrosynthesis reaction architecture, retrosynthesis reactions on molecular representation information respectively corresponding to the four sample molecules S1, S2, S3, and S4 for which the workload node is responsible, to obtain costs respectively corresponding to S1, S2, S3, and S4, which are denoted as cost1, cost2, cost3, and cost4, and transmits the molecular representation information respectively corresponding to S1, S2, S3, and S4 and the costs respectively corresponding to S1, S2, S3, and S4 to the control node. The workload node W2 respectively performs, according to the cost dictionary P0 and the preset retrosynthesis reaction architecture, retrosynthesis reactions on molecular representation information respectively corresponding to the five sample molecules S12, S13, . . . , and S16 for which the workload node is responsible, to obtain costs respectively corresponding to S12, S13, . . . , and S16, which are denoted as cost12, cost13, . . . , and cost16, and transmits the molecular representation information respectively corresponding to S12. S13, . . . , and S16 and the costs respectively corresponding to S12, S13 . . . . , and S16 to the control node, and so on. The workload node W4 respectively performs, according to the cost dictionary P0 and the preset retrosynthesis reaction architecture, retrosynthesis reactions on molecular representation information respectively corresponding to the four sample molecules S17, S18, S19, and S20 for which the workload node is responsible, to obtain costs respectively corresponding to S17, S18, S19, and S20, which are denoted as cost17, cost18, . . . , and cost20), and transmits the molecular representation information respectively corresponding to S17, S18, S19, and S20 and the costs respectively corresponding to S17, S18, S19, and S20 to the control node. Next, the control node updates the cost dictionary P0 according to the received molecular representation information of the sample molecules and the costs respectively corresponding to the sample molecules to obtain an updated cost dictionary P1, and uses the cost dictionary P1 as a current cost dictionary. That is, the cost dictionary P1 is a current cost dictionary in the subsequent second training process.

In the second training process, the current first cost dictionary is P1. In this case, P1 is first transmitted to each of the workload nodes W1, W2, W3, and W4. The workload nodes W1, W2, W3, and W4 respectively perform, according to the preset retrosynthesis reaction architecture, retrosynthesis reactions on the simplified molecular-input line-entry systems of the sample molecules for which the workload nodes are responsible, to obtain the costs respectively corresponding to the sample molecules, and transmit the molecular representation information of the sample molecules and the costs of the sample molecules to the control node. This processing procedure is similar to the processing procedure in the first training process described above, and details are not described herein again. Next, the control node updates the cost dictionary P1 according to the received molecular representation information of the sample molecules and the costs respectively corresponding to the sample molecules to obtain an updated cost dictionary P2, and uses the cost dictionary P2 as a current cost dictionary. That is, the cost dictionary P2 is a current cost dictionary in the subsequent third training process.

According to the above training process, the subsequent third training, the fourth training, . . . , and the $N^{th}$ training are continued until the predetermined condition is met, and the iterative performing of step S2 and step S3 is stopped. That is, the training is completed. After the training is completed, the first cost dictionary updated in response to the predetermined condition being satisfied is determined as the sample cost dictionary.

Figure 2:
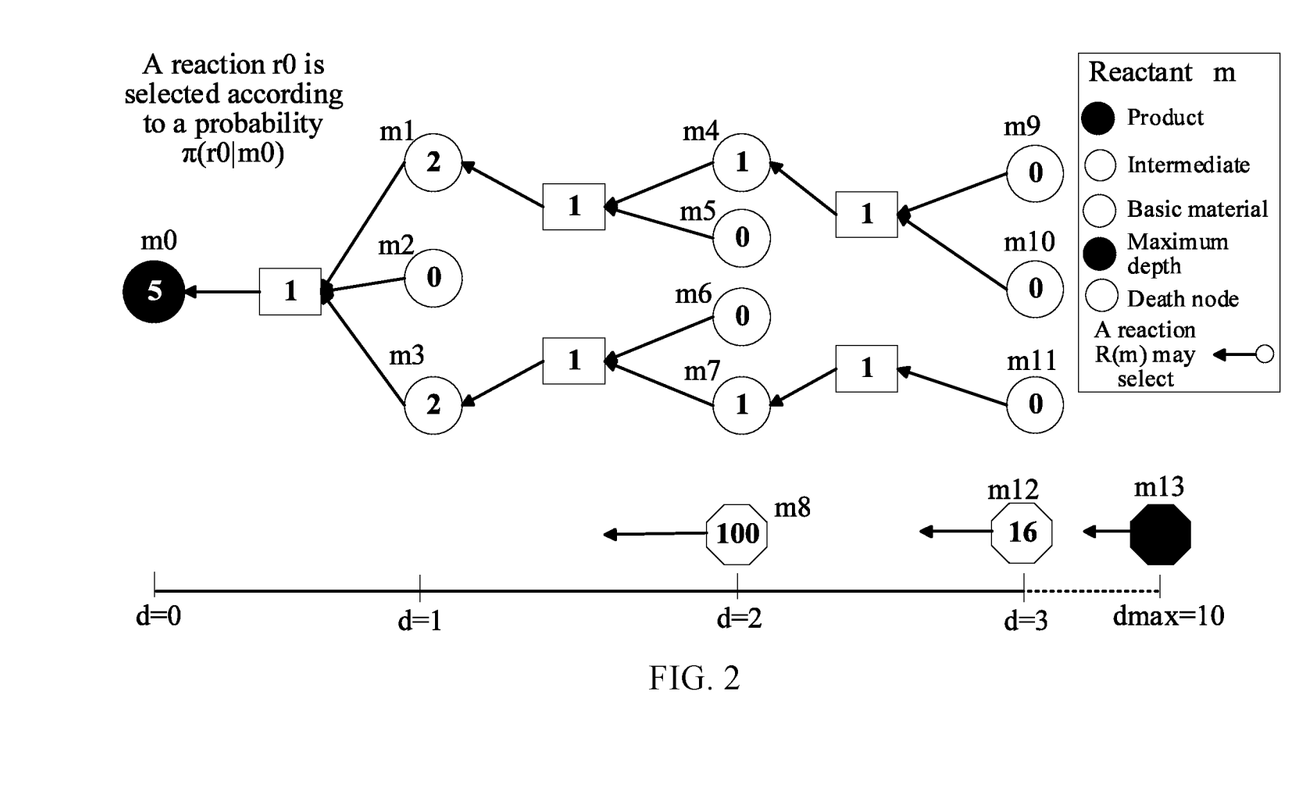
FIG. 2 is a schematic diagram of a retrosynthesis reaction architecture according to an embodiment of this application.

For example, the workload node performs, according to the current first cost dictionary and the multi-step retrosynthesis route shown in FIG. 2, a multi-step retrosynthesis reaction on the simplified molecular-input line-entry system of the sample molecule for which the workload node is responsible, which is actually gradually expanded according to the multi-step retrosynthesis route shown in FIG. 2. During the expansion of a current step, a reaction template is selected according to the current first cost dictionary, and the current step is then displayed according to the reaction template. The expansion process is defined as a retrosynthesis process. m indicates the target molecule, and B is a collection of molecules (about 300,000 species) available with a unit price less than US$100/gram. R(m) is a collection of reactions, and each of the reactions in the collection contains m as a product. π(r|m) is a probability of selecting a reaction r∈ R(m) to use in the synthesis. $c_{rxn}$(r) is a cost of performing the selected reaction r. $c_{sub}$(m') is an available reactant m', m' E B. The total cost $c_{tot}$ of the synthesis reaction may be defined as the following Equation (1).

$$c_{tot} = \sum_r c_{rxn}(r) + \sum_m c_{sub}(m) \quad (1)$$

$c_{rxn}$(r) is the cost of performing the selected reaction r, and $c_{sub}$(m) is an available reactant m.

The total cost of the synthesis reaction is evaluated in all reactions rand all leaf nodes m. Therefore, the deep reinforcement learning technology seeks an optimal value function strategy π to minimize a long-term cumulative return $v_\pi$(m) of the reactant m, as shown in the following Equation (2):

$$v_\pi(m) = \sum_{r \in R(m)} \pi(r|m) \left[ c_{rxn}(r) + \sum_{m' \in M(r)} v_\pi(m') \right] \quad (2)$$

π(r|m) is the probability of selecting the reaction r∈ R(m) to use in the synthesis, $c_{rxn}$(r) is the cost of performing the selected reaction r, and $v_\pi$(m') is a minimized long-term cumulative return of the reactant m'.

The iterative function shown in Equation (2) ends when the target molecule is split into obtainable molecules, that is, $v_\pi(m)=c_{sub}(m)$, which is unrelated to the value function strategy.

For example, the expansion process generates and upgrades a value function strategy, as shown in the following Equation (3), to determine a synthesis route with the least synthesis cost.

$$v_*(m) = \min_r \left[ c_{rxn}(r) + \sum_{m' \in M(r)} v_*(m') \right] \quad (3)$$

$v_*$(m) is a minimized long-term cumulative return of the reactant m according to the upgraded value function strategy, $c_{rxn}$(r) is the cost of performing the selected reaction r, and $v_*$(m') is a minimized long-term cumulative return of the reactant m' according to the upgraded value function strategy.

During actual expansion, a cost 0 indicates an available molecule, a cost 100 indicates a non-existent molecule, and a cost 10 indicates exceeding a maximum depth 10 of the tree. After each round of expansion, the value function strategy is updated, and the value function strategy can be upgraded through value iteration, as shown in the following Equation (4):

$$\pi'(r|m) = \begin{cases} 1, & \text{if } r = \argmin_{r \in R(m)} \left[ c_{rxn}(r) + \sum_{m' \in M(r)} v_\pi(m') \right] \\ 0, & \text{otherwise} \end{cases} \quad (4)$$

π'(r|m) is a probability of selecting the reaction r∈R(m) to use in the synthesis after the upgrade, $c_{rxn}(r)$ is the cost of performing the selected reaction r, and $v_\pi(m')$ is a minimized long-term cumulative return of the reactant m'.

For example, since the expansion process is complicated and time-consuming, it is necessary to adopt a distributed parallel computing method to expand different target molecules at the same time, to obtain costs of the target molecules.

In this embodiment of this application, in the process of performing the plurality of times of retrosynthesis reaction training on each of the plurality of sample molecules concurrently according to the preset retrosynthesis reaction architecture by using the predetermined work cluster, to generate the sample cost dictionary, the control node is mainly responsible for transmitting the target molecule and updating the cost dictionary, and the workload node is responsible for receiving and expanding the target molecule. Because it is necessary to select a reaction template in the expansion process, each workload node needs to maintain the updated cost dictionary after the previous training as the basis for selecting the reaction template by the workload node. In addition, each workload node further needs to store a data set of available molecules to facilitate instant access to the reactants.

For example, during iteratively performing steps S2 and S3, when the predetermined condition is met, the training ends. For example, when the training reaches a predetermined quantity of times (such as 4000 times or 6000 times), the predetermined condition may be considered to be satisfied: and when a difference between a first mean value and a second average value is less than or equal to a predetermined threshold, the predetermined condition may also be considered to be satisfied. The first mean value is a mean value of costs of the plurality of sample molecules obtained by respectively performing $M^{th}$ retrosynthesis reaction training on the plurality of sample molecules according to the preset retrosynthesis reaction architecture by using the plurality of workload nodes of the predetermined work cluster. The second mean value is a mean value of costs of the plurality of sample molecules obtained by respectively performing (M−1)th retrosynthesis reaction training on the plurality of sample molecules according to the preset retrosynthesis reaction architecture by using the plurality of workload nodes of the predetermined work cluster, M being a positive integer greater than 1.

In an example, assuming that M is 6, that is, M−1 is 5, and there are 20 sample molecules (namely, S1, S2, . . . , S20) in total, costs of the sample molecules obtained after the fifth retrosynthesis reaction training are respectively cost1_5, cost2_5, . . . , and cost20_5, and a mean value V_5 of the costs of the 20 sample molecules may be (cost1_5+cost2_5+ . . . +cost20_5)/20. The costs of the sample molecules obtained after the sixth retrosynthesis reaction training are respectively cost1_6, cost2_6, . . . , and cost20_6, and a mean value V_6 of the costs of the 20 sample molecules may be (cost1_6+cost2_6+ . . . +cost20_6)/20. When a difference between V_6 and V_5 is less than or equal to a predetermined threshold (such as 0.1 or 15%), it is considered that the predetermined condition is met.

In this embodiment of this application, when the predetermined retrosynthesis reaction architecture includes multi-step retrosynthesis reactions, the multi-step retrosynthesis reactions may be respectively performed, according to a current first cost dictionary and the preset retrosynthesis reaction architecture by using the plurality of workload nodes, on the molecular representation information of the sample molecules that respectively correspond to the plurality of workload nodes, until available molecules respectively corresponding to the sample molecules are obtained, or a retrosynthesis reaction in a first predetermined step is performed.

For example, when the retrosynthesis reaction is performed on molecular representation information of a first sample molecule (for example, a sample molecule S1) corresponding to each workload node (for example, the workload node W1) according to the preset retrosynthesis reaction architecture by using the workload node, it is actually performing reciprocating iteration in accordance with the preset retrosynthesis reaction architecture. Each iteration is to perform retrosynthesis decomposition on the sample molecule (for example, the sample molecule S1), until an available molecule is obtained through the decomposition or a maximum depth is performed (that is, a retrosynthesis reaction in the first predetermined step is performed), That is, the retrosynthesis reaction of the entire sample molecule is completed through the multi-step retrosynthesis reaction. Upon completion of a retrosynthesis reaction in a step, a reaction product of the retrosynthesis reaction in the step may be searched for in a pre-stored available molecule library. When the reaction product is found in the available molecule library, it indicates that the reaction product is an available molecule. In this case, the retrosynthesis reaction may be ended. That is, the retrosynthesis reaction of the target molecule is completed. Molecular representation information of the sample molecule and a cost of the retrosynthesis reaction in the current step in which the reaction product is an available molecule are transmitted to the control node together. When the reaction product is not found in the available molecule library, it indicates that the reaction product is not an available molecule. In this case, a retrosynthesis reaction in a next step can be performed.

For example, in a process of continuously performing a retrosynthesis reaction in a next step, if the corresponding reaction product has not been found in the available molecular library, it is not suitable for performing the retrosynthesis reaction in the next step indefinitely. In this case, a predetermined step (that is, the first predetermined step) such as the 10th step or the 15th step may be set. After a retrosynthesis reaction in the predetermined step (such as the 10th step) of is performed, and a reaction product generated by performing the retrosynthesis reaction in the predetermined step (such as the 10th step) is still not found in the available molecular library, the retrosynthesis reaction is ended, and the molecular representation information of the sample molecule and a cost obtained by performing the retrosynthesis reaction in the predetermined step (that is, the 10th step) are together transmitted to the control node.

In this embodiment of this application, in the process of respectively performing, according to a current first cost dictionary and the preset retrosynthesis reaction architecture by using the plurality of workload nodes, retrosynthesis reactions on the molecular representation information of the sample molecules that respectively correspond to the workload nodes, each of the workload nodes determines, for the molecular representation information of the sample molecule that corresponds to the workload node and the retrosynthesis reaction in each step in the preset retrosynthesis reaction architecture, a retrosynthesis reaction template corresponding to the retrosynthesis reaction in the step according to the current first cost dictionary, and performs the retrosynthesis reaction in the step according to the determined retrosynthesis reaction template.

For example, in the process in which each workload node (for example, the workload node W1) performs a retrosynthesis reaction in each step (such as the first step) on the molecular representation information of the first sample molecule (for example, the sample molecule S1) corresponding to the workload node according to the current first cost dictionary (for example, the cost dictionary P1) and the preset retrosynthesis reaction architecture, a retrosynthesis template (for example, a template M1) corresponding to the retrosynthesis reaction in the first step is first determined according to the cost dictionary P1 based on the molecular representation information of the sample molecule S1. Next, the retrosynthesis reaction in the first step is performed on the molecular representation information of the sample molecule S1 according to the template M1. Upon completion of the retrosynthesis reaction in the first step, if a reaction product obtained in the retrosynthesis reaction in the first step is not in the available molecule library, a retrosynthesis reaction in the second step continues to be performed. In a process of performing the retrosynthesis reaction in the second step, retrosynthesis reaction template (such as a template M2) corresponding to the retrosynthesis reaction in the second step also can be determined based on the molecular representation information of the sample molecule S1 according to the cost dictionary P1, and the retrosynthesis reaction in the second step is performed on the molecular representation information of the sample molecule S1 according to the template M2, and so on. Retrosynthesis reactions in subsequent steps are processed in the same manner as the first step and the second step. Details are not described herein again.

In this embodiment of this application, after the sample cost dictionary training is completed, the retrosynthesis route design of the multi-step retrosynthesis reaction may be performed on molecules with key values in the cost dictionary. However, for new molecules that are not currently in the sample cost dictionary, the retrosynthesis route design of the retrosynthesis reaction is not yet possible. Therefore, the predetermined neural network may be trained according to the pre-generated sample cost dictionary, to obtain the target neural network, so that the fitting ability and generalization ability of the neural network can be fully utilized. For the target molecule with a key value in the sample cost dictionary or a new molecule, retrosynthesis process may be performed on a target molecule by using the target neural network, to obtain the corresponding retrosynthesis route and a retrosynthesis reaction in each step.

For example, because the pre-generated sample cost dictionary stores the key-value pair formed by the molecular representation information of each of the sample molecules and the cost of the sample molecule, and cannot be directly applied to the predetermined neural network, data processing may be first performed on the pre-generated sample cost dictionary, to convert the key-value pair formed by the molecular representation information of each of the sample molecules and the cost of the sample molecule in the pre-generated sample cost dictionary into a sample data set in a data form that matches the predetermined neural network, and the predetermined training network is then trained based on the sample data set to obtain the target neural network. Equivalently, the key-value pairs stored in the sample cost dictionary (that is, the key-value pairs between the molecular representation information of the sample molecules and the costs of the sample molecules) are distilled and extracted into the predetermined neural network to obtain the target neural network, so that the target neural network obtains the ability to estimate a cost of any molecule and the ability to design retrosynthetic routes for similar molecules.

Figure 3:
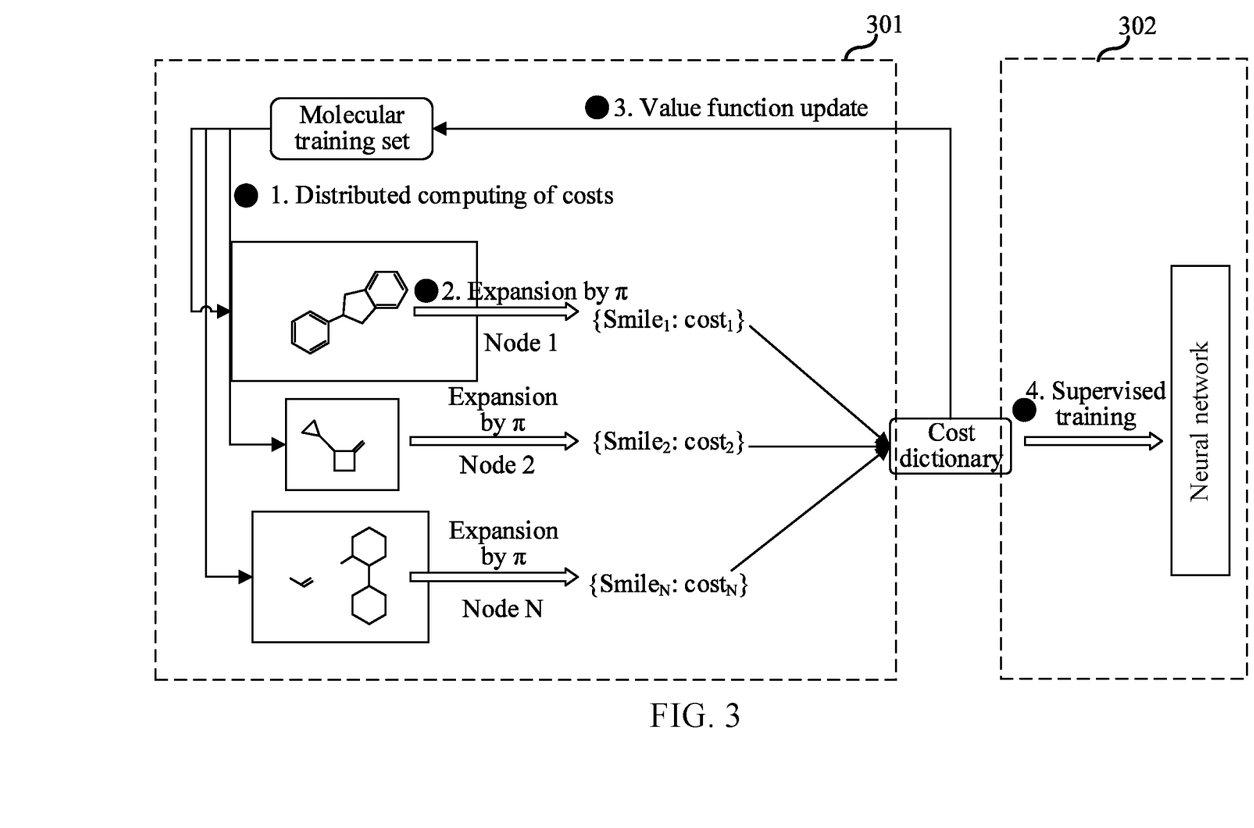
FIG. 3 is a schematic diagram of a process of generating a sample cost dictionary and a target neural network according to an embodiment of this application.

For example, FIG. 3 is a schematic diagram of generating the sample cost dictionary and performing supervised training for a neural network according to an embodiment of this application. In FIG. 3, the left half part 301 is a schematic diagram (that is, calculation of distributed costs) of performing a plurality of times of retrosynthesis reaction training on each of a plurality of sample molecules concurrently in a distributed manner according to a preset retrosynthesis reaction architecture, to generate the sample cost dictionary. The right half part 302 is a schematic diagram of performing supervised training for the neural network according to the sample cost dictionary. A molecular training set in FIG. 3 is a set of sample molecules that includes the plurality of sample molecules. A node 1, a node 2, and a node N are a plurality of workload nodes. The character Smile represents a calculation function, and the character cost represents a cost of a retrosynthesis reaction.

In a process of generating the sample cost dictionary in FIG. 3, a distributed training architecture is adopted to transmit simplified molecular-input line-entry systems (that is, molecular representation information) of all sample molecules to different workload nodes (node 1, node 2, and node N) by using a control node. Each of the workload nodes is responsible for the calculation of costs of some of the sample molecules. In the first round of iterative training, after the workload node receives a message about its own load, the workload node expands a corresponding sample molecule according to the manner shown in FIG. 2, and a cost of the sample molecule in the current cost dictionary is finally obtained. Next, after the workload node completes calculation, the workload node returns the sample molecule and its cost. Finally, the control node collects all the sample molecules and costs and updates the cost dictionary. In addition, a current value function strategy is updated according to the cost dictionary. The cost dictionary is equivalent to the value function strategy. Next, the second round of iterative training is performed, which is similar to the first round of iterative training, and the details are not described herein again. A plurality of rounds of iteration are repeated. After the training for the cost dictionary is completed, a current retrosynthesis strategy is obtained.

Next, after an updated cost dictionary is obtained through a plurality of rounds of training, supervised training may be performed on the predetermined neural network according to the updated cost dictionary based on a deep learning technology, and a neural network capable of designing a retrosynthesis route for molecules (that is, the target neural network) is finally obtained.

In practical application, a detailed process of distributed computing includes the following steps.

(1). Smile transmission: the simplified molecular-input line-entry systems (that is, the molecular representation information) of the plurality of sample molecules in the molecule training set are respectively transmitted to the workload nodes (that is, backup nodes) through the control node (that is, a master node). The backup nodes respectively perform processing by using the simplified molecular-input line-entry systems as inputted parameters of the calculation function.

(2). Single sample molecule expansion: After receiving the simplified molecular-input line-entry systems, the backup nodes perform expansion according to the current cost dictionary to obtain the expansion process.

(3). Expansion result receiving and update of the cost dictionary: The master node receives costs obtained by the backup nodes according to the expansion process and the simplified molecular-input line-entry systems of the corresponding sample molecules, and updates the cost dictionary according to the received simplified molecular-input line-entry systems the sample molecules and the costs of the sample molecules.

(4). New cost dictionary transmission: After updating the cost dictionary, the master node transmits the updated cost dictionary to the backup nodes before a next iteration.

(5). Regular training of the neural network: The finally updated cost dictionary is transmitted to the neural network through data processing, data set division and training.

For example, the plurality of times of retrosynthesis reaction training are respectively performed on the plurality of sample molecules concurrently according to the preset retrosynthesis reaction architecture in a distributed manner to accelerate the training. However, once the training is completed, deployment may be easily performed on a personal computer, and searching time of the synthetic route inferred by the neural network is also very short, which has strong practicability.

In this embodiment of this application, the following steps may be performed to input the molecular representation information into the target neural network and perform retrosynthesis processing on the target molecule, to obtain a retrosynthesis reaction in each step of the retrosynthesis processing on the target molecule.

Step A1: Determine, for a current step during the retrosynthesis processing, at least one candidate reaction template according to the molecular representation information, and determine a target reaction template from the at least one candidate reaction template.

Step A2: Perform retrosynthesis processing of the current step according to the target reaction template to obtain a retrosynthesis reaction in the current step.

Step A3: Iteratively perform step A1 and step A2 until an available molecule of the target molecule is obtained or retrosynthesis processing of a second predetermined step is performed, and output the retrosynthesis reaction in each step of the retrosynthesis processing on the target molecule.

For example, performing the retrosynthesis processing including performing multiple steps of retrosynthesis reactions on the molecular representation information of the target molecule (for example, a molecule T1) using the target neural network. For a current reaction step in the retrosynthesis processing (that is, retrosynthesis processing of the current step), at least one candidate reaction template (for example, temp1, temp2, or temp3) may be determined according to molecular representation information of the molecule T1. The target reaction template is determined from the at least one candidate reaction template, and retrosynthesis processing of the current step is then performed according to the target reaction template, so as to obtain a retrosynthesis reaction in the current step. The current step is each step in the retrosynthesis processing. When the retrosynthesis processing includes six steps, in performing retrosynthesis processing of the first step, the first step is the current step in the retrosynthesis processing. In performing retrosynthesis processing of the second step, the second step is the current step in the retrosynthesis processing, and so on. In performing retrosynthesis processing of the sixth step, the sixth step is the current step in the retrosynthesis processing.

For example, the retrosynthesis processing on the target molecule (for example, the molecule T1) performed by using the target neural network is actually to perform a multi-step retrosynthesis reaction on the target molecule T1. The retrosynthesis reaction in each step is equivalent to decomposition of the target molecule until an available molecule is obtained or the second predetermined step is performed. The retrosynthesis reaction of the entire target molecule is completed through the multi-step retrosynthesis processing. Upon completion of a retrosynthesis reaction in a step, a reaction product of the retrosynthesis reaction in the step may be searched for in the pre-stored available molecule library. When the reaction product is found in the available molecule library, it indicates that the reaction product is an available molecule. In this case, the retrosynthesis reaction may be ended. That is, the retrosynthesis reaction of the target molecule is completed. When the reaction product is not found in the available molecule library, it indicates that the reaction product is not an available molecule. In this case, a retrosynthesis reaction in a next step can continue to be performed.

For example, in a process of continuously performing a retrosynthesis reaction in a next step, if the corresponding reaction product has not been found in the available molecular library, it is not suitable for performing the retrosynthesis reaction in the next step indefinitely. In this case, a predetermined step (that is, the second predetermined step) such as the 5th step or the 8th step may be set. After a retrosynthesis reaction in the predetermined step (such as the 5th step) is performed, and a reaction product generated by performing the retrosynthesis reaction in the predetermined step (such as the 5th step) is still not found in the available molecular library, the retrosynthesis reaction is ended, and the retrosynthesis reaction in each step is outputted. That is, the retrosynthesis reaction in the first step, the retrosynthesis reaction in the second step, . . . , and the retrosynthesis reaction in the fifth step are outputted.

In this embodiment of this application, in determining the target reaction template according to the at least one candidate reaction template, retrosynthesis processing of the current step may be performed on the molecular representation information according to each of the candidate reaction templates, so as to obtain a reaction precursor corresponding to the candidate reaction template. Next, a cost corresponding to each reaction precursor is determined, and the candidate reaction template corresponding to the smallest cost is determined as the target reaction template.

For example, for the current step (such as the second step) of the retrosynthesis processing, at least one candidate reaction template (for example, six candidate reaction templates) may be selected according to the molecular representation information of the target molecule by using a template screening network. Next, according to each of the candidate reaction templates, retrosynthesis processing of the current step is performed on the molecular representation information to obtain a corresponding reaction precursor, which is equivalent to expanding the candidate reaction template to obtain a reaction precursor. Next, a cost of the reaction precursor of each candidate reaction template is estimated by using a cost estimation network, to obtain the cost of the reaction precursor. Next, the candidate reaction template corresponding to the smallest cost (that is, the candidate reaction template with the lowest cost value) is selected as the target reaction template of the current step.

The above template screening network is equivalent to a template database and stores various reaction templates. The above cost estimation network is generated through supervised training according to the pre-generated sample cost dictionary, which is similar to the above target neural network.

Through experiment validation, the retrosynthesis processing in this embodiment of this application has the following advantages.

1. Distributed retrosynthesis training can be significantly accelerated. The single-machine version of multi-step retrosynthesis training requires 25 CPU cores for one month of training at a time, while the distributed multi-step retrosynthesis training only requires about one day to complete the training based on 50 16-core CPU work clusters, which has obvious acceleration effects, thereby greatly improving the iteration efficiency and training progress.

2. The retrosynthesis route of existing molecules can be well designed. Most of the retrosynthesis design schemes have been validated by chemical experts, and a given retrosynthesis route is more flexible and effective, reducing unnecessary branching reactions.

3. In this embodiment of this application, a retrosynthesis route can be designed for a new molecule, which has great reference value and achieves the purpose of assisted design. For a retrosynthesis route difficult for chemistry experts to design before, this embodiment can give possible potential retrosynthesis schemes and also inspire the design ideas of chemistry experts without being affected by the misunderstandings and limitations of thinking.

4. Compared with the method of manual searching, this method has the huge advantages of large-scale commercial application and shortening a development cycle of new drugs.

Figure 4:
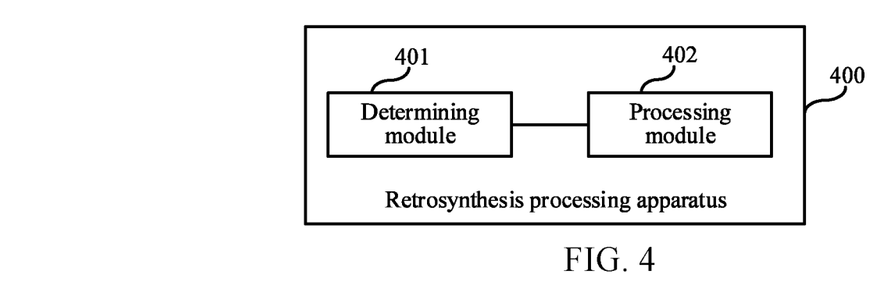
FIG. 4 is a schematic diagram of a basic structure of a retrosynthesis processing apparatus according to an embodiment of this application.

FIG. 4 is a schematic structural diagram of a retrosynthesis processing apparatus according to another embodiment of this application. As shown in FIG. 4, the device 400 may include a determining module 401 and a processing module 402.

The determining module 401 is configured to determine molecular representation information of a target molecule.

The processing module 402 is configured to input the molecular representation information into a target neural network, and perform retrosynthesis processing on the target molecule based on the molecular representation information of the target molecule, to obtain a retrosynthesis reaction in each step of the retrosynthesis processing on the target molecule, the target neural network being obtained by training a predetermined neural network according to a generated sample cost dictionary, the sample cost dictionary being generated by performing a plurality of times of retrosynthesis reaction training on each of a plurality of sample molecules concurrently, and a retrosynthesis reaction being performed according to a preset retrosynthesis reaction architecture.

In this embodiment of this application, the device 400 includes a first training module configured to perform the plurality of times of retrosynthesis reaction training on each of the plurality of sample molecules concurrently according to the preset retrosynthesis reaction architecture by using the predetermined work cluster, to generate the sample cost dictionary. The predetermined work cluster includes a plurality of workload nodes and at least one control node, the workload node corresponds to at least one electronic device, and the control node corresponds to at least one electronic device.

The first training module is further configured to distribute molecular representation information respectively corresponding to the plurality of sample molecules to the plurality of workload nodes by using the at least one control node: and iteratively perform the following steps: respectively performing, according to a current first cost dictionary and the preset retrosynthesis reaction architecture by using the plurality of workload nodes, retrosynthesis reactions on the molecular representation information of the sample molecules that respectively correspond to the workload nodes, to obtain costs respectively corresponding to the sample molecules, and transmitting the molecular representation information of the sample molecules and the costs of the sample molecules to the at least one control node, the current first cost dictionary including a key-value pair formed by the molecular representation information of each of the sample molecules and the cost of the sample molecule: updating the current first cost dictionary according to the molecular representation information of the plurality of sample molecules and the costs respectively corresponding to the plurality of sample molecules by using the at least one control node; and determining, when a predetermined condition is satisfied, the first cost dictionary updated in response to the predetermined condition being satisfied as the sample cost dictionary.

In this embodiment of this application, that the predetermined condition is satisfied includes any one of the following: a predetermined quantity of times of training are performed: or a difference between a first mean value and a second mean value is less than or equal to a predetermined threshold, the first mean value being a mean value of costs of the plurality of sample molecules obtained by respectively performing $M^{th}$ retrosynthesis reaction training on the plurality of sample molecules according to the preset retrosynthesis reaction architecture by using the plurality of workload nodes of the predetermined work cluster, and the second mean value being a mean value of costs of the plurality of sample molecules obtained by respectively performing $(M-1)^{th}$ retrosynthesis reaction training on the plurality of sample molecules according to the preset retrosynthesis reaction architecture by using the plurality of workload nodes of the predetermined work cluster, M being a positive integer greater than 1.

In this embodiment of this application, the preset retrosynthesis reaction architecture includes multi-step retrosynthesis reactions. The first training module is further configured to: respectively perform the multi-step retrosynthesis reactions according to the preset retrosynthesis reaction architecture, until available molecules respectively corresponding to the sample molecules are obtained, or a retrosynthesis reaction in a first predetermined step is performed.

In this embodiment of this application, the first training module is further configured to: determine, according to the retrosynthesis reaction in each step in the preset retrosynthesis reaction architecture and the current first cost dictionary by each of the workload nodes for the molecular representation information of the sample molecule that corresponds to the workload node, a retrosynthesis reaction template corresponding to the retrosynthesis reaction in the step, and perform the retrosynthesis reaction in the step according to the determined retrosynthesis reaction template.

In this embodiment of this application, the device 400 includes a second training module configured to perform data processing on the generated sample cost dictionary, and convert a key-value pair formed by the molecular representation information of each of the sample molecules and the cost of the sample molecule in the generated sample cost dictionary into a sample data set in a data form that matches the predetermined neural network: and train the predetermined training network based on the sample data set to obtain the target neural network.

In this embodiment of this application, the processing module 402 is further configured to iteratively perform the following steps: determining at least one candidate reaction template for a current step in the retrosynthesis processing according to the molecular representation information of the target molecule, and determining a target reaction template from the at least one candidate reaction template: performing retrosynthesis processing of the current step according to the target reaction template to obtain a retrosynthesis reaction in the current step: and outputting the retrosynthesis reaction in each step of the retrosynthesis processing on the target molecule when an available molecule of the target molecule is obtained or retrosynthesis processing of a second predetermined step is performed.

In this embodiment of this application, the processing module 402 is further configured to: perform retrosynthesis processing of the current step on the molecular representation information of the target molecule according to each of the at least one candidate reaction template, so as to obtain a reaction precursor respectively corresponding to the candidate reaction template: and determine a cost corresponding to each reaction precursor, and determine the candidate reaction template corresponding to the smallest cost as the target reaction template.

In the embodiment of this application, the molecular representation information includes a simplified molecular-input line-entry system or a molecular graph.

According to the device provided in this embodiment of this application, the sample cost dictionary is generated by performing the plurality of times of retrosynthesis reaction training on each of the plurality of sample molecules concurrently according to the preset retrosynthesis reaction architecture, thereby implementing a distributed parallel computing scheme for training optimization of the sample cost dictionary, which greatly reduces the time for training optimization of the sample cost dictionary, increases the calculation speed and improves iteration efficiency, so that a value function strategy can be quickly obtained according to the sample cost dictionary, greatly reducing the time for calculation of the value function strategy. The predetermined neural network is trained according to the pre-generated sample cost dictionary to obtain the target neural network, so that costs of retrosynthesis reactions can be fitted through the neural network to obtain a retrosynthesis reaction in each step. In addition, it is ensured that the target neural network can provide an effective retrosynthesis route when performing retrosynthesis processing on the target molecule, to accurately obtain the retrosynthesis reaction in each step, thereby implementing the automated design of the retrosynthesis route. Moreover, the pre-generated cost dictionary is mapped to the neural network, which can make full use of the fitting ability and generalization ability of the neural network, so that a reasonable and effective retrosynthesis route can be designed for new molecules, and the retrosynthesis reaction in each step can be obtained.

This embodiment is an apparatus embodiment corresponding to the foregoing method embodiment, and this embodiment may be implemented in combination with the foregoing method embodiment. Related technical details mentioned in the foregoing method embodiment are still valid in this embodiment, and in order to reduce repetition, details are not described herein again. Correspondingly, related technical details mentioned in this embodiment may also be applied to the foregoing method embodiment.

Figure 5:
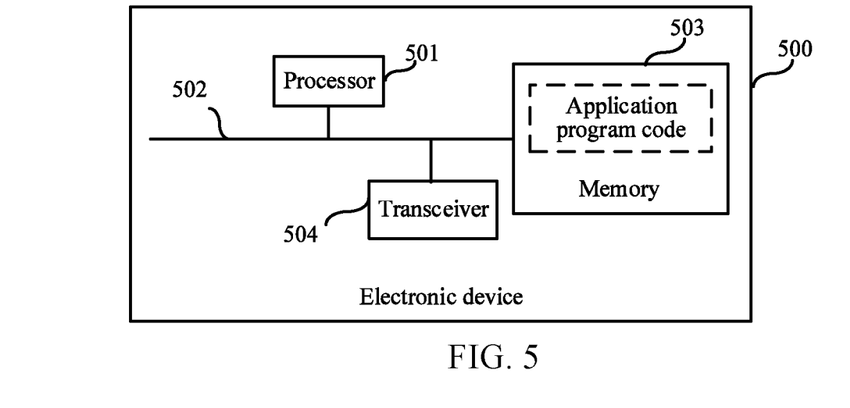
FIG. 5 is a schematic structural diagram of an electronic device according to another embodiment of this application.

Another embodiment of this application provides an electronic device (e.g., a computer device) for implementing the foregoing retrosynthesis processing method. The foregoing control node and workload nodes may be implemented by the electronic device. The electronic device may be various types of terminal devices or servers. The server may be an independent physical server, or may be a server cluster or a distributed system including a plurality of physical servers. As shown in FIG. 5, an electronic device 500 includes a processor 501 and a memory 503. The processor 501 and the memory 503 are connected, for example, are connected by using a bus 502. Further, the electronic device 500 may further include a transceiver 504. In an actual application, there may be one or more transceivers 504. The structure of the electronic device 500 does not constitute a limitation on this embodiment of this application.

The processor 501 is applied in this embodiment of this application, and is configured to implement the functions of the determining module and the processing module shown in FIG. 4. The transceiver 504 includes a receiver and a transmitter.

The processor 501 may be a central processing unit (CPU), a general-purpose processor, a digital signal processor (DSP), an application-specific integrated circuit (ASIC), a field programmable gate array (FPGA) or another programmable logic device, a transistor logic device, a hardware component, or any combination thereof. The processor 901 may implement or perform various examples of logic blocks, modules, and circuits described with reference to content disclosed in this application. The processor 501 may also be a combination that implements computing functions, for example, including a combination of one or more microprocessors or a combination of a DSP and a microprocessor.

The bus 502 may include a channel, to transmit information between the foregoing components. The bus 502 may be a PCI bus, an EISA bus, or the like. The bus 502 may be classified into an address bus, a data bus, a control bus, and the like. For ease of description, the bus in FIG. 5 is represented by using only one bold line, but it does not indicate that there is only one bus or one type of bus.

The memory 503 may be a ROM or another type of static storage device that can store static information and a static instruction: or a RAM or another type of dynamic storage device that can store information and an instruction: or may be an EEPROM, a CD-ROM or another compact-disc storage medium, optical disc storage medium (including a compact disc, a laser disk, an optical disc, a digital versatile disc, a Blu-ray disc, or the like) and magnetic disk storage medium, another magnetic storage device, or any other medium that can be configured to carry or store expected program code in a form of an instruction or a data structure and that is accessible by a computer, but is not limited thereto.

The memory 503 is configured to store application program code for performing the solutions of this application, and is controlled and executed by the processor 501. The processor 501 is configured to execute the application program code stored in the memory 503, to implement the actions of the retrosynthesis processing apparatus provided in the embodiment shown in FIG. 4.

The electronic device provided in this embodiment of this application includes a memory, a processor, and a computer program stored in the memory and executable by the processor, the program, when executed by the processor, causing the processor to: determine molecular representation information of a target molecule: then input the molecular representation information into a target neural network, and perform retrosynthesis processing on the target molecule, to obtain a retrosynthesis reaction in each step of the retrosynthesis processing on the target molecule. The target neural network is obtained by training a predetermined neural network according to a pre-generated sample cost dictionary. The sample cost dictionary is generated by performing a plurality of times of retrosynthesis reaction training on each of a plurality of sample molecules concurrently according to a preset retrosynthesis reaction architecture.

An embodiment of this application provides a non-transitory computer-readable storage medium, storing a computer program, the program, when executed by a processor, causing the processor to implement the method according to the foregoing embodiments. A sample cost dictionary is generated by performing a plurality of times of retrosynthesis reaction training on each of a plurality of sample molecules concurrently according to a preset retrosynthesis reaction architecture, thereby implementing a distributed parallel computing scheme for training optimization of the sample cost dictionary, which greatly reduces the time for training optimization of the sample cost dictionary, increases the calculation speed and improves iteration efficiency, so that a value function strategy can be quickly obtained according to the sample cost dictionary, greatly reducing the time for calculation of the value function strategy. The predetermined neural network is trained according to the pre-generated sample cost dictionary to obtain a target neural network, so that costs of retrosynthesis reactions can be fitted through the neural network to obtain a retrosynthesis reaction in each step. In addition, it is ensured that the target neural network can provide an effective retrosynthesis route when performing retrosynthesis processing on the target molecule, to accurately obtain the retrosynthesis reaction in each step, thereby implementing the automated design of the retrosynthesis route. Moreover, the pre-generated cost dictionary is mapped to the neural network, which can make full use of the fitting ability and generalization ability of the neural network, so that a reasonable and effective retrosynthesis route can be designed for new molecules, and the retrosynthesis reaction in each step can be obtained.

The computer-readable storage medium provided in this embodiment of this application is applied to any one embodiment of the foregoing method.

It is to be understood that, although the steps in the flowchart in the accompanying drawings are sequentially shown according to indication of an arrow, the steps are not necessarily sequentially performed according to a sequence indicated by the arrow. Unless explicitly specified in this specification, execution of the steps is not strictly limited in the sequence, and the steps may be performed in other sequences. In addition, at least some steps in the flowcharts in the accompanying drawings may include a plurality of substeps or a plurality of stages. The substeps or the stages are not necessarily performed at the same moment, but may be performed at different moments. The substeps or the stages are not necessarily performed in sequence, but may be performed in turn or alternately with another step or at least some of substeps or stages of the another step.

The foregoing descriptions are some implementations of this application. A person of ordinary skill in the art may make several improvements and refinements without departing from the principle of this application, and the improvements and refinements shall fall within the protection scope of this application.

Note that the various embodiments described above can be combined with any other embodiments described herein.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

As used herein, the term "unit" or "module" refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit. The division of the foregoing functional modules is merely used as an example for description when the systems, devices, and apparatus provided in the foregoing embodiments performs retrosynthesis processing and/or determines molecular representation information. In practical application, the foregoing functions may be allocated to and completed by different functional modules according to requirements, that is, an inner structure of a device is divided into different functional modules to implement all or a part of the functions described above.

What is claimed is:

1. A method performed by at least one computer device, the method comprising:
   determining molecular representation information of a target molecule;
   inputting the molecular representation information into a target neural network; and
   performing, via the target neural network, retrosynthesis processing on the target molecule based on the molecular representation information of the target molecule, to obtain a respective retrosynthesis reaction of the target molecule for each step of the retrosynthesis processing, wherein the target neural network is obtained by training a predetermined neural network according to a sample cost dictionary that is generated by concurrently performing retrosynthesis reaction training on each of a plurality of sample molecules, and the respective retrosynthesis reaction is performed according to a preset retrosynthesis reaction architecture.

2. The method according to claim 1, further comprising:
   prior to inputting the molecular representation information into the target neural network:
   concurrently performing the retrosynthesis reaction training on each of the plurality of sample molecules using a predetermined work cluster, to generate the sample cost dictionary, wherein the predetermined work cluster comprises a plurality of workload nodes and at least one control node, the workload nodes and the control node being implemented by the at least one computer device.

3. The method according to claim 2, wherein concurrently performing the retrosynthesis reaction training on each of the plurality of sample molecules further comprises:

distributing respective molecular representation information corresponding to the plurality of sample molecules to the plurality of workload nodes by using the at least one control node; and iteratively performing the following operations:
performing, according to a current first cost dictionary and the preset retrosynthesis reaction architecture using the plurality of workload nodes, retrosynthesis reactions on the molecular representation information of respective sample molecules that correspond to the respective workload nodes, to obtain respective costs corresponding to the respective sample molecules, and transmitting the molecular representation information of the respective sample molecules and the respective costs of the sample molecules to the at least one control node, wherein the current first cost dictionary comprises a key-value pair formed by the molecular representation information of each of the sample molecules and the cost of the sample molecule;

updating the current first cost dictionary according to the molecular representation information of the plurality of sample molecules and the respective costs corresponding to the plurality of sample molecules by using the at least one control node; and determining, when a predetermined condition is satisfied, the first cost dictionary updated in response to the predetermined condition being satisfied as the sample cost dictionary.

4. The method according to claim 3, wherein the predetermined condition is satisfied when:
a predetermined number of times of training are performed; or
a difference between a first mean value and a second mean value is less than or equal to a predetermined threshold, the first mean value being a mean value of costs of the plurality of sample molecules obtained by respectively performing $M^{th}$ retrosynthesis reaction training on the plurality of sample molecules according to the preset retrosynthesis reaction architecture using the plurality of workload nodes of the predetermined work cluster, and the second mean value being a mean value of costs of the plurality of sample molecules obtained by respectively performing $(M-1)^{th}$ retrosynthesis reaction training on the plurality of sample molecules according to the preset retrosynthesis reaction architecture using the plurality of workload nodes of the predetermined work cluster, wherein M is a positive integer greater than one.

5. The method according to claim 3, wherein:
the preset retrosynthesis reaction architecture comprises multiple steps of retrosynthesis reactions; and
performing retrosynthesis reactions according to the preset retrosynthesis reaction architecture comprises:
respectively performing the multiple steps of retrosynthesis reactions according to the preset retrosynthesis reaction architecture, until available molecules corresponding to the sample molecules are obtained, or a retrosynthesis reaction in a first predetermined step is performed.

6. The method according to claim 4, wherein performing, according to the current first cost dictionary and the preset retrosynthesis reaction architecture using the plurality of workload nodes, the retrosynthesis reactions further comprises:
determining, according to the retrosynthesis reaction in each step in the preset retrosynthesis reaction architecture and the current first cost dictionary by each of the workload nodes for the molecular representation information of the sample molecule that corresponds to the workload node, a retrosynthesis reaction template corresponding to the retrosynthesis reaction in the step, and performing the retrosynthesis reaction in the step according to the determined retrosynthesis reaction template.

7. The method according to claim 1, further comprising prior to inputting the molecular representation information into the target neural network:
performing data processing on the generated sample cost dictionary;
converting a key-value pair formed by molecular representation information of each of the sample molecules and a cost of the sample molecule in the generated sample cost dictionary into a sample data set in a data form that matches the predetermined neural network; and
training the predetermined training network based on the sample data set to obtain the target neural network.

8. The method according to claim 1, wherein performing retrosynthesis processing on the target molecule further comprises iteratively performing the following operations:
determining at least one candidate reaction template for a current step in the retrosynthesis processing according to the molecular representation information of the target molecule;
determining a target reaction template from the at least one candidate reaction template;
performing retrosynthesis processing of the current step according to the target reaction template to obtain a retrosynthesis reaction in the current step; and
outputting the retrosynthesis reaction in each step of the retrosynthesis processing performed on the target molecule in a case that an available molecule of the target molecule is obtained or retrosynthesis processing of a second predetermined step is performed.

9. The method according to claim 8, wherein determining the target reaction template from the at least one candidate reaction template further comprises:
performing retrosynthesis processing of the current step on the molecular representation information of the target molecule according to each of the at least one candidate reaction template, to obtain a reaction precursor corresponding to the candidate reaction template; and
determining a cost corresponding to the reaction precursor, and determining the candidate reaction template corresponding to the smallest cost as the target reaction template.

10. The method according to claim 1, wherein the molecular representation information comprises a simplified molecular-input line-entry system or a molecular graph.

* * * * *

UNITED STATES PATENT AND TRADEMARK OFFICE
CERTIFICATE OF CORRECTION

Page 1 of 1

PATENT NO. : 12,027,240 B2
APPLICATION NO. : 17/522702
DATED : July 2, 2024
INVENTOR(S) : Yaodong Yang et al.

It is certified that error appears in the above-identified patent and that said Letters Patent is hereby corrected as shown below:

On the Title Page

(54) and in the Specification, Column 1, Lines 1-3, please delete "ELECTRONIC DEVICE, AND COMPUTER-READABLE STORAGE MEDIUM" and insert --RETROSYNTHESIS PROCESSING METHOD AND APPARATUS, ELECTRONIC DEVICE, AND COMPUTER-READABLE STORAGE MEDIUM--.

Signed and Sealed this
Sixth Day of August, 2024

Katherine Kelly Vidal
*Director of the United States Patent and Trademark Office*